US010323221B2

(12) United States Patent
Nguyen et al.

(10) Patent No.: US 10,323,221 B2
(45) Date of Patent: Jun. 18, 2019

(54) DEVICE FOR CONTROLLED APICAL FLOW IN CELL CULTURE INSERTS

(71) Applicants: Northeastern University, Boston, MA (US); Massachusetts Institute of Technology, Cambridge, MA (US)

(72) Inventors: Transon V. Nguyen, San Francisco, CA (US); Collin D. J. Edington, Cambridge, MA (US); Emily C. Suter, Boston, MA (US); Rebecca Lyn Carrier, Needham, MA (US); David L. Trumper, Plaistow, NH (US); Linda G. Griffith, Cambridge, MA (US)

(73) Assignees: Northeastern University, Boston, MA (US); Massachusetts Institute of Technology, Cambridge, MA (US)

( * ) Notice: Subject to any disclaimer, the term of this patent is extended or adjusted under 35 U.S.C. 154(b) by 164 days.

(21) Appl. No.: 15/399,496

(22) Filed: Jan. 5, 2017

(65) Prior Publication Data

US 2017/0306278 A1    Oct. 26, 2017

Related U.S. Application Data

(60) Provisional application No. 62/275,331, filed on Jan. 6, 2016.

(51) Int. Cl.
| | |
|---|---|
| *C12M 1/00* | (2006.01) |
| *C12M 1/12* | (2006.01) |
| *C12M 1/34* | (2006.01) |
| *C12M 3/00* | (2006.01) |
| *C12M 3/06* | (2006.01) |

(52) U.S. Cl.
CPC ............... *C12M 3/06* (2013.01); *C12M 23/02* (2013.01); *C12M 23/34* (2013.01); *C12M 23/40* (2013.01); *C12M 23/44* (2013.01); *C12M 25/04* (2013.01); *C12M 27/18* (2013.01); *C12M 29/14* (2013.01); *C12M 41/00* (2013.01)

(58) Field of Classification Search
CPC ........ C12M 3/06; C12M 23/02; C12M 23/34; C12M 23/40; C12M 41/00; C12M 27/18; C12M 25/04; C12M 29/14; C12M 23/44
See application file for complete search history.

(56) References Cited

U.S. PATENT DOCUMENTS

| | | | | |
|---|---|---|---|---|
| 5,139,951 A | * | 8/1992 | Butz et al. ............. | C12M 23/00 422/552 |
| 2005/0014129 A1 | * | 1/2005 | Cliffel et al. ........ | G01N 33/5005 435/4 |
| 2007/0166817 A1 | * | 7/2007 | Wilkes et al. ......... | C12M 25/04 435/297.5 |

(Continued)

*Primary Examiner* — Gautam Prakash
(74) *Attorney, Agent, or Firm* — Hamilton, Brook, Smith & Reynolds, P.C.

(57) ABSTRACT

A device for controlling apical flow to a cell culture includes an apical insert that defines at least one inlet channel extending from an inlet port to an apical feed port and at least one outlet channel extending from an apical effluent port to an outlet port. The apical insert includes a projecting portion configured to extend into a cell culture insert to a depth that is less than a depth of the cell culture insert, and a contact surface configured to maintain a spatial relationship between the projecting portion and the cell culture insert.

18 Claims, 10 Drawing Sheets

(56) References Cited

U.S. PATENT DOCUMENTS

2013/0022500 A1\* 1/2013 Angeloni Suter et al. .................. C12M 25/04 422/82.01
2014/0363883 A1\* 12/2014 Hayes et al. ........... C12M 25/04 435/288.7
2015/0276713 A1\* 10/2015 Wortelboer et al. ......................... B01L 3/5021 435/7.92

\* cited by examiner

DEVICE FOR CONTROLLED APICAL FLOW IN CELL CULTURE INSERTS

RELATED APPLICATION

This application claims the benefit of U.S. Provisional Application No. 62/275,331, filed on Jan. 6, 2016. The entire teachings of the above application are incorporated herein by reference.

GOVERNMENT SUPPORT

This invention was made with government support under W911NF-12-2-0039 from DARPA. The government has certain rights in the invention.

BACKGROUND

Cell culture inserts, such as hanging cell culture inserts, are used in conjunction with well plates for the growth and differentiation of various cell types. Cell culture inserts provide access to both apical and basal domains of the cell culture, making it possible to study both sides of a cell monolayer or to study a co-culture of two or more cell types, by creating a biomimicry boundary. However, it can be difficult to control conditions at the apical domain of a cell culture insert. Any manipulation at the apical domain, such as by, for example, providing media to the cell culture, typically requires exposing at least the apical surface of the cell culture to the environment, thereby risking exposure to contaminants. In addition, the direct application of a fluid to the apical surface of a cell culture can result in uneven distribution of the fluid over the cell layer and can cause physical disturbance to the cells themselves.

Specialized cell culture systems have been developed that can provide more precise control of fluid flow to apical and basal surfaces of a cell culture. However, such specialized cell culture systems, which include custom-shaped wells, flow chambers, and cell culture channels, are fully integrated systems that are often incompatible with other cell culture equipment. Such systems can also be harder to operate than conventional hanging cell culture inserts because cell seeding is not as straightforward as seeding with an open insert, which is the common practice in most labs. Additionally, hanging cell culture inserts are more widely available and more frequently used by researchers than such specialized cell culture systems.

SUMMARY OF THE INVENTION

There exists a need for a device that can control apical flow to a cell culture that is grown in a cell culture insert, such as a hanging cell culture insert or other cell culture insert which permits a cell culture to be grown in a suspended environment relative to a well plate.

Accordingly, an apical insert is provided that can control flow of a fluid to an apical domain of a cell culture. The apical insert includes a projecting portion configured to extend into a cell culture insert to a depth that is less than a depth of the cell culture insert. The apical insert also includes a contact surface configured to maintain a spatial relationship between the projecting portion of the apical insert and the cell culture insert. At least one inlet channel and at least one outlet channel are defined by the apical insert. The inlet channel extends from an inlet port to an apical feed port, and the outlet channel extends from an apical effluent port to an outlet port. The projecting portion of the apical insert can be, for example, a cylindrical boss.

The apical insert can include various configurations of apical feed ports and effluent ports to control flow to the apical domain. In particular, the apical feed port and the apical effluent port can be located at an outer periphery of the projecting portion of the apical insert, thereby providing an indirect flow of fluid from the inlet channel to the apical surface of the cell culture insert. Alternatively, the apical feed port and the apical effluent port can be located at an apical surface of the projecting portion of the apical insert, thereby providing a direct flow of fluid from the inlet channel to the apical surface of the cell culture insert. The apical insert can include two or more apical feed ports, and each apical feed port can be located at a different location at the projecting portion. For example, at least one of the apical feed ports can be located at an outer periphery of the protecting portion and the other of the apical feed ports can be located at an apical surface of the projecting portion. Alternatively, or in addition, each of the apical feed ports can be located at a different depth at an outer periphery of the projecting portion.

The apical insert can also include two or more effluent ports. For example, the apical insert can include a plurality of apical feed ports and a plurality of apical effluent ports. The plurality of apical feed ports and plurality of apical effluent ports can be interspersed at an apical surface of the projecting portion, similar to a showerhead, and providing or retrieving an even distribution of media or other fluid to the apical domain.

The apical insert, in addition to controlling flow, can also provide a sealed apical chamber for preventing contamination of the cell culture. For example, the apical insert can include a seal coupled to the projecting portion and configured to seal the projecting portion against an inner perimeter of the cell culture insert. Alternatively, or in addition, the apical insert can include a seal coupled to the contact surface and configured to seal the contact surface against a flange of the cell culture insert.

Various sensors can also be coupled to the projecting portion of the apical insert. Such sensors can be configured to sense a biological condition at the apical surface of the cell culture insert, such as, for example, temperature, oxygen concentration, pH, transepithelial electrical resistance, and the like.

A system for controlling apical flow to a cell culture includes a cell culture insert, an apical insert, and at least one seal configured to seal the apical insert against the cell culture insert. The system can also include at least one valve in fluidic communication with the inlet port and configured to control flow of a fluid through the inlet channel of the apical insert. Alternatively, or in addition, at least one pump can be included in the system. The pump can be in in fluidic communication with the inlet port, the outlet port, or both and configured to control flow of a fluid through an apical volume defined by the projecting portion and the cell culture insert The system can also include a controller configured to control flow of a fluid through an apical chamber defined by the projecting portion and the cell culture insert through control of at least one valve or at least one pump. The valve(s) or pump(s) can be in fluidic communication with the inlet port, the outlet port, or both. The controller, through control of the valve(s) and/or pump(s), can be configured to supply a flow of a fluid with a substantially even velocity profile across an apical surface of the cell culture insert.

The system can also include at least one sensor coupled to the apical insert and configured to sense a biological condition at an apical surface of the cell culture insert and a controller in communication with the sensor. The controller can be configured to cause a valve or pump, in fluidic communication with the inlet port or outlet port, to change state as a function of a representation of the biological condition output by the at least one sensor.

A system for controlling apical flow to a cell culture can include means for culturing cells across a biomimicry boundary, means for delivering a fluid to an apical surface of the biomimicry boundary with a substantially even velocity profile across the apical surface, and means for sealing an apical volume having a boundary defined by the apical surface of the biomimicry boundary.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

Apical flow devices and systems are provided that are configured to deliver controlled flow of a fluid to an apical domain of a cell culture insert, such as a hanging cell culture insert or a supported cell culture insert. Hanging cell culture inserts are often used in creating in vitro models of complex cell systems, such as the gastrointestinal system. For example, a monolayer of enterocytes can be grown in a conventional cell culture dish to model an epithelium layer of the small intestine; however, such a cell culture does not produce an accurate model of the barrier function of the gastrointestinal tract. To recapitulate the barrier function of the gastrointestinal tract, a more physiologically accurate model can be created by adding goblet cells above the enterocytes to produce mucus, as is present at the luminal side of the small intestine, and by adding immune cells beneath the enterocytes to model the lamina propria of the intestinal tissue. The immune component strongly contributes to the barrier function of the small intestine, as it must prevent pathogenic microorganisms from crossing the epithelium and entering the bloodstream. Hanging cell culture inserts can be used in conjunction with well plates to co-culture various cell types in various configurations, such as the stack of goblet cells, enterocytes, and immune cells described above, to provide for more accurate modeling of a physiological system.

Figure 1:
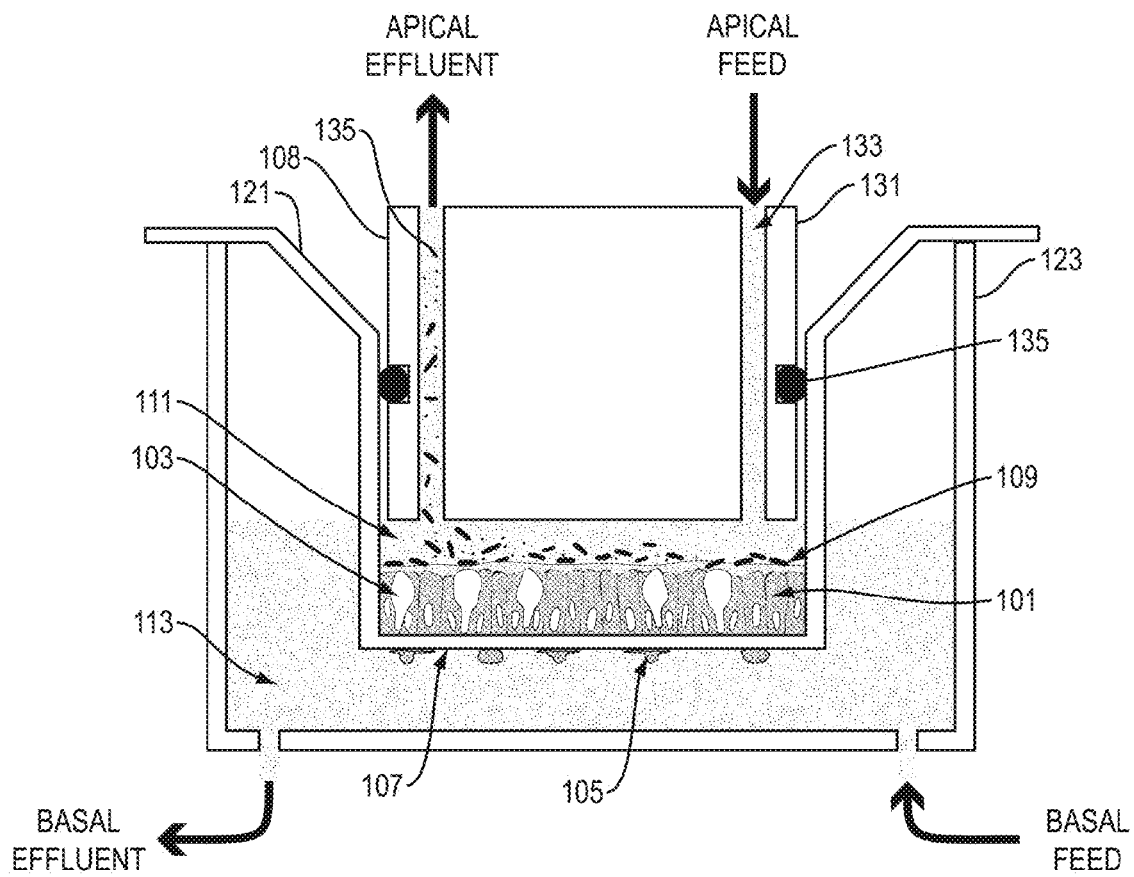
FIG. 1 is a schematic of a hanging cell culture grown in a hanging cell culture insert with an apical insert providing media flow to the cell culture.

An example of a hanging cell culture to model the small intestine is shown in FIG. 1. Specifically, a co-culture of enterocytes 101 and mucus-producing goblet-like cells 103 are grown on the apical side 111 of a membrane 107 of a hanging cell culture insert 121, while macrophages 105 are seeded on the basal side 113. Thus, the apical media is analogous to a lumenal environment of the small intestine, while the basal media is analogous to systemic circulation. The hanging cell culture insert 121 can be placed in a well 123 of a cell-culture plate. Optionally, the well 123 can allow for basal media flow.

In vivo, conditions are different on each side of an epithelium layer. Typically, tissue near the intestinal wall is oxygenated as a result of the proximity to blood vessels within the lamina propria and submucosa. As oxygen diffuses through the epithelium and into the lumen, it is consumed by immune cells, enterocytes, microbes near the epithelium, and any other aerobic constituents in the diffusion path. As a result of this dense concentration of oxygen-consuming species, oxygen tension quickly decreases as one moves from the submucosal layer to the lumen, to the point where the environment is nearly anoxic 1 mm away from the epithelium.

Accordingly, to properly model the barrier function of the gut, a decreasing oxygen gradient should be maintained, with the apical environment being relatively oxygen-poor and the basal environment being relatively oxygen-rich. However, it is difficult to maintain control over an oxygen gradient in a conventional hanging cell culture insert, which is generally open to the environment, particularly at the apical side of the co-culture. Other conditions, such as temperature and the presence or absence of other fluids (e.g., gases, liquids) can also be difficult to maintain with a hanging cell culture insert, such as insert 121.

Returning to FIG. 1, an apical insert 131 is provided which extends into the hanging cell culture insert 121. The apical insert 131 extends to a depth that is less than the depth of the hanging cell culture insert 121, so as to not disturb the enterocytes 101 and goblet cells 103 of the tissue model. Apical insert 131 can be used to control conditions at the apical environment of the co-culture by controlling the flow of various fluids. Apical flow in this tissue model serves not only as a means for media replenishment, but also for microbe population control, as well as mucin shearing to maintain a relatively constant mucin concentration. For example, various microbe strains, represented by microbes 109, that are representative of an in vivo microbiome can be introduced through an inlet channel 133 defined by the apical insert 131 and, together with mucin 108, expelled through an outlet channel 135, which is also defined by the apical insert 131. Apical insert 131 can also include a seal 135 to seal against the hanging cell culture insert 121. Seal 135 can restrict the surrounding environment from affecting the tissue model. Apical insert 121 can thus allow for reduced oxygen tension in the cell culture media by providing a controlled flow of oxygen. Because the cell/microbe culture consumes oxygen faster than oxygen can diffuse into the media through the basal side, increased oxygen tension is often a problem with hanging cell culture inserts. Depending on the balance of oxygen consumption and diffusion, a microenvironment that more closely recapitulates the hypoxic domain within the lumen of the small intestine can be achieved with use of the apical insert 121.

Apical inserts of the present invention can be configured to integrate with hanging cell culture inserts, such as hanging cell culture insert 121, which are widely available and are commonly used in research and development laboratories. Hanging cell culture inserts include Transwell® Permeable Supports (Corning, Inc., Tewksbury, Mass.), Millicell® Cell Culture Inserts (EMD Millipore, Billerica, Mass.), and ThinCert™ Cell Culture Inserts (Greiner Bio-One Inc., Monroe, N.C.). Apical inserts of the present invention can also be configured to integrate with cell culture inserts that permit a cell culture to be grown in a suspended state relative to a well plate and that are supported by other means. For example, some cell culture inserts are supported by feet which rest against a surface of the well plate, rather than by a flange which rests against an upper surface of the well plate.

Figure 2A:
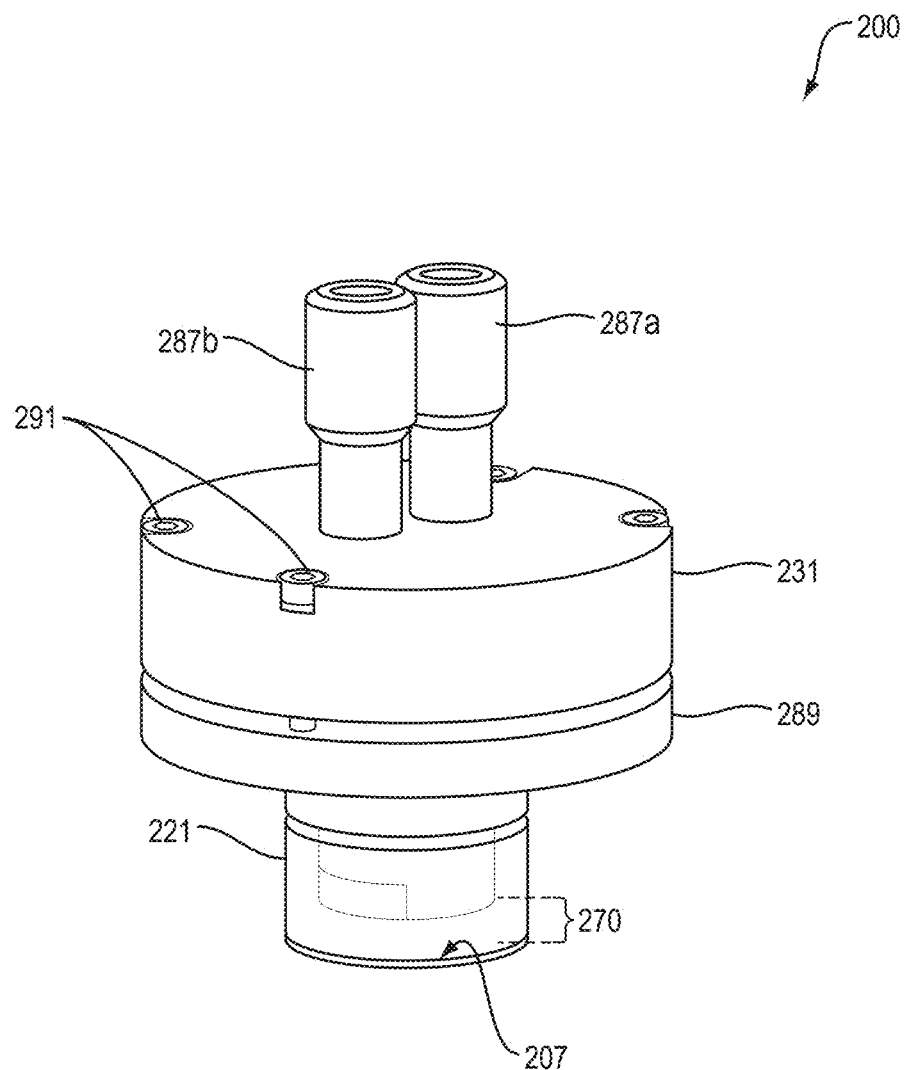
FIG. 2A is a perspective view of an apical insert assembled together with a hanging cell culture insert.
Figure 2B:
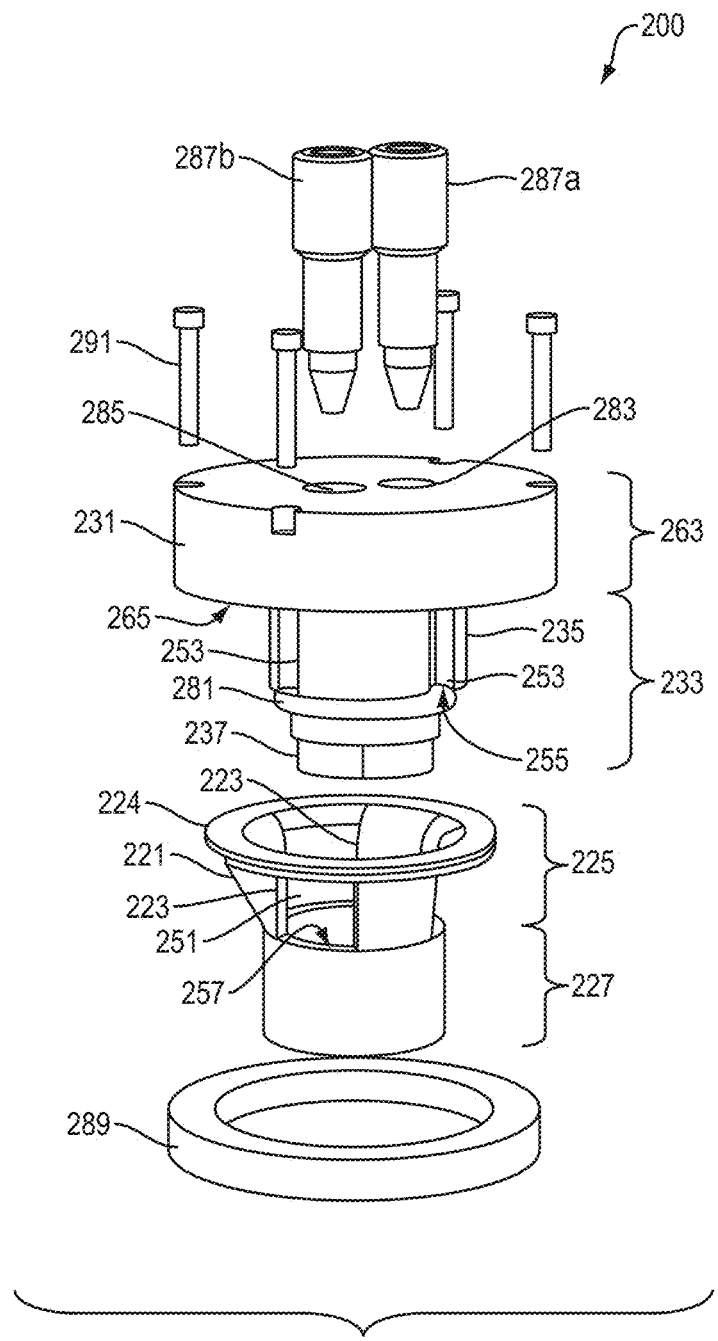
FIG. 2B is an exploded view of the apical insert assembly of FIG. 3A.

An apical insert system 200 is shown in FIGS. 2A-2B. The apical insert 231 includes a projecting portion 233 configured to extend into the hanging cell culture insert 221 to a depth that is less than a depth of the hanging cell culture insert. As shown in FIG. 2B, the projecting portion 233 can include a first region 235 and a second region 237, with each region configured to engage with a portion of hanging cell culture insert 221. More specifically, first region 235 is configured to extend through an upper portion 225 of the hanging cell culture insert 221, and second region 237 is configured to extend into a lower, solid-wall cylindrical portion 227 of the hanging cell culture insert 221. As illustrated in FIGS. 2A-2B, hanging cell culture insert 221 is representative of a Transwell insert. An upper portion 225 of the Transwell hanging cell culture insert 221 includes supports 223, which extend between the lower cylindrical portion 227 and a flange 224. Supports 223 and associated structure, such as gaps 251, are particular to a Transwell hanging cell culture insert, while other hanging cell culture inserts may include different features. Supports 223 are provided in Transwell inserts to assist with locating the Transwell insert toward the center of a well and to assist with user handling by providing structures that are easily grasped with tweezers.

Accordingly, as illustrated in FIGS. 2A and 2B, the first region 235 of the apical insert 231 includes features to engage with supports 223 and gaps 251 of the Transwell hanging cell culture insert. In particular, first region 235 includes ridged portions 253, which are configured to engage with gaps 251. Ridged portions 253 can provide a first contact surface 255 configured to contact a surface 257 created by gaps 251. This first contact surface 255 can thus be configured to maintain a spatial relationship between the projecting portion 233 and the hanging cell culture insert 221. A second contact surface 265 can also be provided on an upper portion 263 of the apical insert 231. The second contact surface 265 can be configured to engage with a surface of flange 224 of hanging cell culture insert 221.

While two contact surfaces are shown and described with respect to FIGS. 2A and 2B, it should be understood that the ridged portions 253, providing contact surface 255, and upper portion 263, providing contact surface 265, are each optional features of an apical insert 231. One or both contact surfaces can be included an apical insert. For example, a hanging cell culture insert other than a Transwell insert may not include structures such as supports 223 and gaps 251. Accordingly, the projecting portion 233 of an apical insert may not include an upper portion 235 having ridges 253. Upper portion 235 can be dimensioned and, optionally, include other structural features such as ridges 253 in varying patterns and sizes, such that it fits within other models of hanging cell culture inserts.

The lower portion 237 of the apical insert 231 can be, for example, a cylindrical boss that projects into an interior space defined by a hanging cell culture insert. First and/or second contact surfaces 255, 265 can ensure that the projecting portion 233 of the apical insert 231 does not collide with a membrane of the hanging cell culture insert 221. As shown in FIG. 2A, a gap 270 can be defined between lower portion 237 and a membrane surface 207 of the hanging cell culture insert 221.

Also included in the apical insert system 200 are optional sealing features. In particular, an interior seal 281 can be located between the upper region 235 and the lower region 237 of apical insert 221. Seal 281 can create a radial seal between the projecting portion 233 of the apical insert 221 and the inner perimeter of the hanging cell culture insert 221. Seal 281 can be, for example, one or more O-rings. A seal can also be created between the upper portion 263 of the apical insert and the flange 224 with a lower ring 289. Screws 291 can engage with upper portion 263 and lower ring 289, to fasten the hanging cell culture insert 221 against the apical insert 231. While two sealing surfaces are shown and described with respect to FIGS. 2A and 2B, it should be understood that one or both or both can be included in an apical insert. For example, seal 281 can be included in a system, while a seal formed between upper portion 263 and flange 224 can be omitted, or vice versa. Upper region 263 and lower ring 289 can also serve as a spacing mechanism to prevent overdetermined contact between the components of the system, as further described below with respect to FIG. 3.

The ridged portions 253 of the apical insert 231 can additionally ensure that the apical insert 231 is rotationally fixed within the hanging cell culture insert 221. Since the apical insert 231 is generally fastened to the lower ring 289 and not directly to the hanging cell culture insert 221, it is possible for the hanging cell culture insert 221 to slip and rotate about its centerline independently of the apical insert 231 and lower ring 289, which is undesirable. The ridged portions 253 can be radial protrusions configured to engage with gaps 251 of, for example, a Transwell type insert. Ridged portions 253 can thereby constrain rotation of the hanging cell culture insert 221 with respect to the apical insert 231.

Apical insert 221 also defines at least one interior channel (FIG. 3), which provides an inlet and/or outlet path for media flow to the apical side of the hanging cell culture insert. As illustrated in FIGS. 2A-2B, two channels 283, 285 are defined by the apical insert 231. Each channel can be configured to receive a compression fitting 287a, 287b, which can allow for further connection to other components, such as tubing, pumps, valves, etc.

Figure 3:
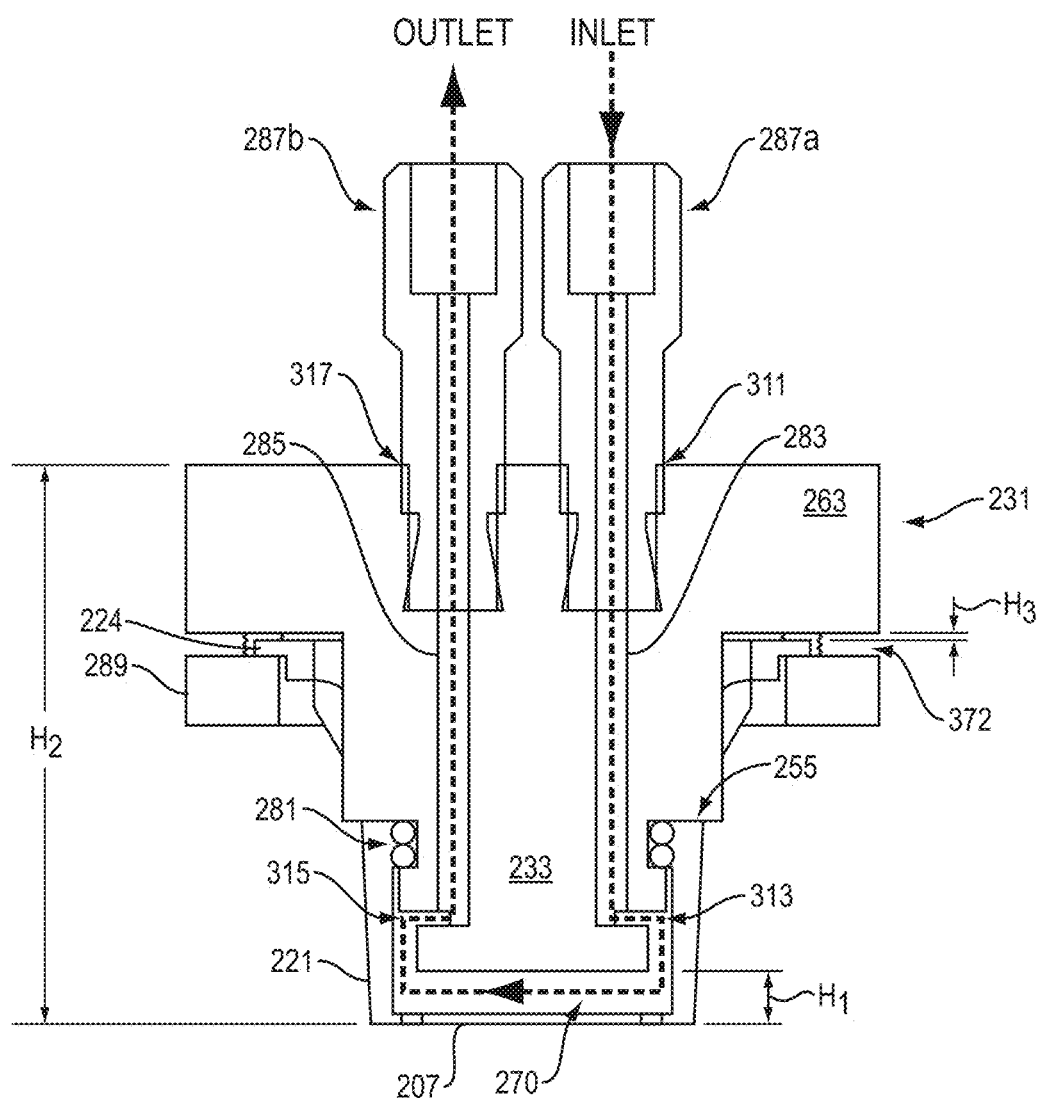
FIG. 3 is a cross-sectional view of an apical insert assembly.

A cross-sectional view of an assembled apical insert system 200 is shown in FIG. 3. Inlet channel 283 extends from an inlet port 311 to an apical feed port 313. Outlet channel 285 extends from an apical effluent port 315 to an outlet port 317. Inlet port 311 and outlet port 317 can be sized to engage with compression fittings 287a, 287b, or, alternatively, tubing, valves, or other elements typically used for providing fluid flow.

A flowpath through apical insert 231 is illustrated in FIG. 3 with a dashed line and arrows. The flowpath includes inlet channel 283, an apical flow channel at gap 270, and outlet channel 285. As illustrated in FIG. 3, the apical feed port 313 and the apical effluent port 315 are located at an outer periphery of the projecting portion 233. Thus, feed is delivered toward an inner wall of the hanging cell culture insert, rather than directly to the apical surface of the membrane, which can provide for a more even flow distribution and less disturbance to a culture of cells grown at membrane 207.

Contact surface 255 maintains a spatial relationship between the projecting portion 233 and the hanging cell culture insert 221, which provides for a gap 270 having a height $H_1$. The height $H_1$ can be of about 5 mm or less, for example, about 4 mm, about 3 mm, about 2 mm, or about 1 mm. Together with the apical feed port 313 and the apical effluent port 315, gap 270 provides for an apical flow channel. The apical flow channel, or apical chamber, is sealed from the environment by the seal 281.

As illustrated in FIG. 3, the upper portion 263 of the apical insert does not directly contact flange 224 of the hanging cell culture insert. A gap 372 having a height $H_3$ is provided to assist in ensuring that the system 200 is not overdetermined by an abundance of contact surfaces. The height $H_3$ can be of about 1 mm or less, for example, about 0.7 mm, about 0.5 mm, or about 0.3 mm. Alternatively, the upper portion 263 can be configured to directly contact flange 224, with or without additional sealing elements, such as an O-ring or other rubberized component, to form a seal instead of, or in addition to, seal 281.

A total height, $H_2$ of the system 200 can be of about 30 mm or less, for example, about 25 mm, about 20 mm, or about 15 mm. The total height $H_2$ can vary depending upon the depth of a hanging cell culture insert and a depth needed to provide for fluid connections to channels 283, 285.

Figure 4A:
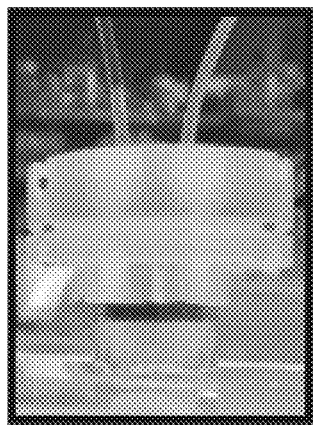
FIG. 4A is a photograph of an apical insert at a first step of flow testing.
Figure 4B:
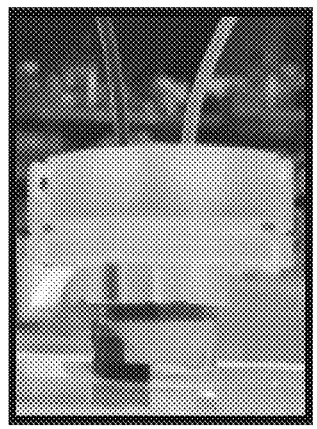
FIG. 4B is a photograph of the apical insert at a second step of flow testing.
Figure 4C:
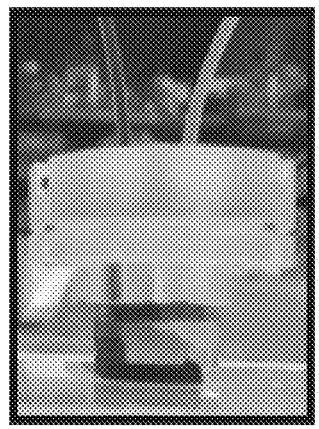
FIG. 4C is a photograph of the apical insert at a third step of flow testing.
Figure 4D:
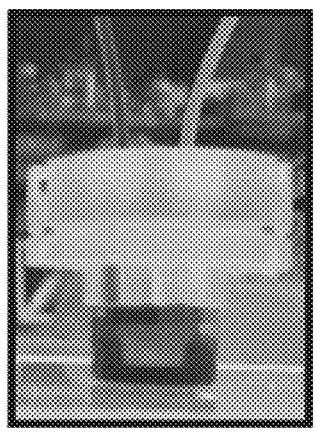
FIG. 4D is a photograph of the apical insert at a fourth step of flow testing.
Figure 4E:
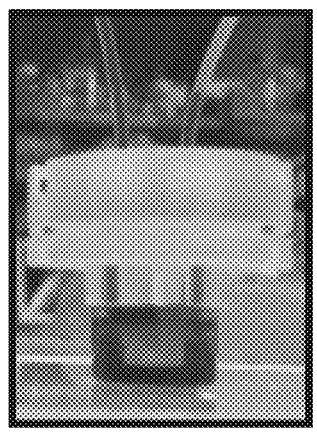
FIG. 4E is a photograph of the apical insert at a fifth step of flow testing.
Figure 4F:
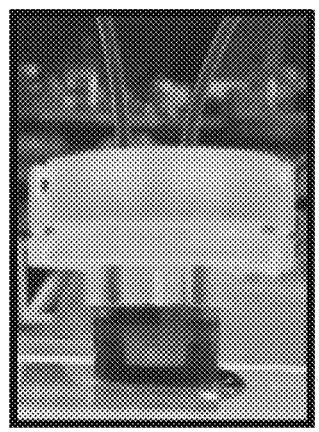
FIG. 4F is a photograph of the apical insert at a sixth step of flow testing.

As described above, the apical feed port 313 and the apical effluent port 315 are located at an outer periphery of the projecting portion 313. The placement of ports 313, 315 can be selected to provide a flow that is fairly even across the apical surface of the hanging cell culture insert 221, which can, in turn, allow for an even distribution of fresh media across cells located in the insert 221. FIGS. 4A-4F include a time series of images of an apical flow system as it is primed with dye in water. The apical flow system of FIGS. 4A-4F includes a port configuration similar to the location of ports 313, 315 illustrated in FIG. 3. It is seen in the time series that the apical flow system successfully self-primes, as no bubbles in the flow path were visible upon inspection. The drop of dye at the bottom of the system in FIG. 4F is due to water slowly leaching through the porous membrane at the bottom of the Transwell hanging cell culture insert. An even flow profile with this geometry is also shown. Over time, as dye is introduced through the inlet, it flows over the apical side of the membrane with a substantially even velocity profile.

Figure 5A:
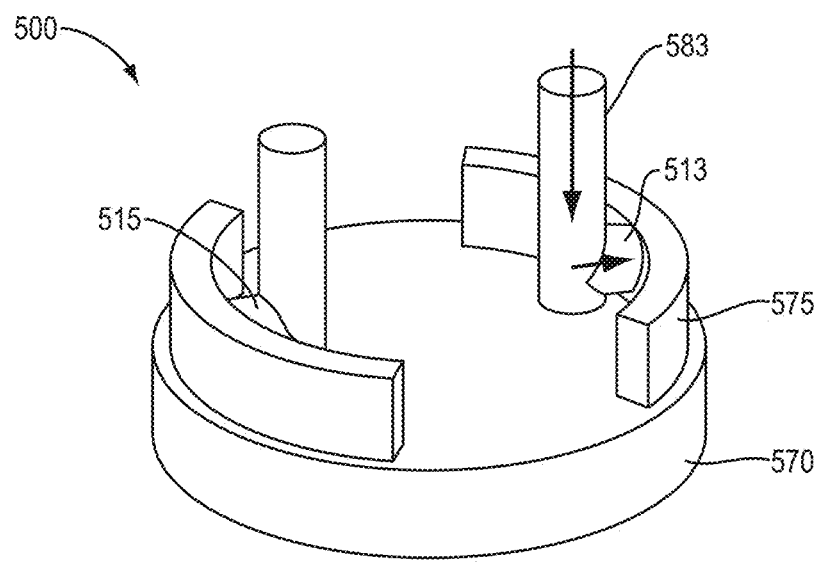
FIG. 5A is a perspective view of an apical domain defined by a portion of an apical insert and a hanging cell culture insert, illustrating an example of a flow geometry from an inlet channel of the apical insert.

Various geometries for port placement within an apical insert can provide for an even flow distribution to the apical side of a hanging cell culture insert. FIGS. 5A-5E illustrate examples of various port configurations. FIG. 5A is a perspective view of an apical domain 500 of an apical insert system, including an inlet channel 583, a horizontal bore providing an apical feed port 513, and a horizontal volume 570 representing part of an apical flow channel (i.e., a gap as defined by a lower surface of an apical insert and a membrane surface of a hanging cell culture insert). As illustrated in FIG. 5A, one apical feed port is provided, which delivers fluid to a vertical volume 575 of an apical flow channel (i.e., a gap as defined by an outer perimeter of the projecting portion of an apical insert and an inner perimeter of a hanging cell culture insert), with the fluid then travelling to the horizontal volume 570. Fluid flow in indicated in FIG. 5A by arrows. A similar configuration can apply to apical effluent port 515.

Figure 5B:
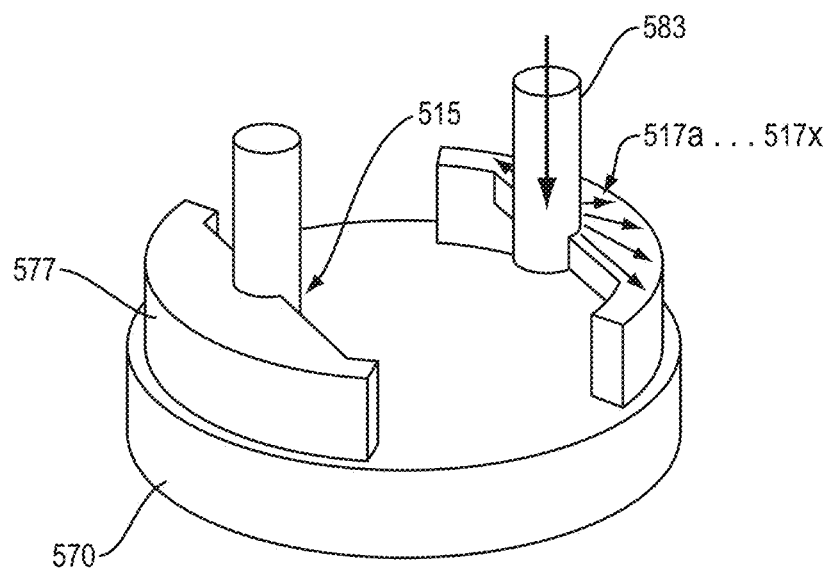
FIG. 5B a perspective view of another example of a flow geometry from an inlet channel of the apical insert.

Alternatively, several apical feed ports can be provided, as illustrated in FIG. 5B. In particular, a number of slots 517a-517x can be provided, with each slot delivering fluid to a different horizontal location within vertical volume 575. A similar configuration can apply to vertical volume 577 at apical effluent port 515.

Figure 5C:
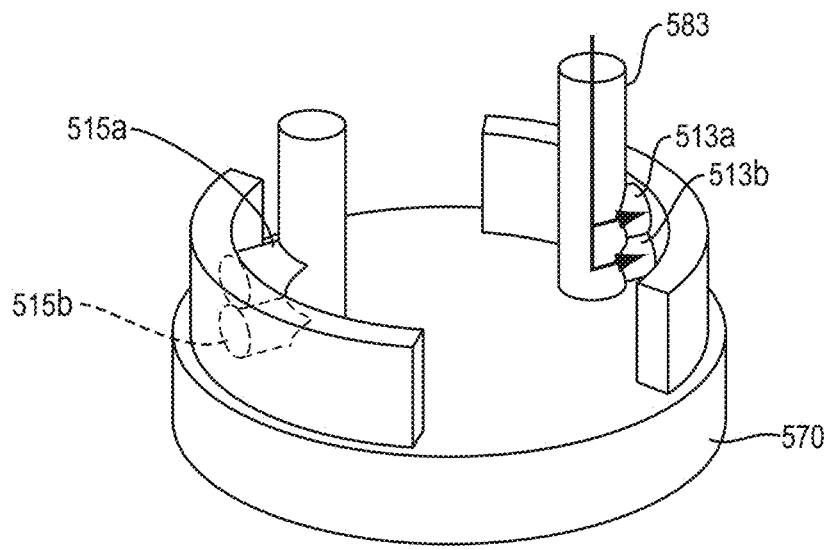
FIG. 5C is a perspective view of an example of a flow geometry from an inlet channel of the apical insert to multiple inlet ports.

In another configuration, at least two apical feed ports 513a, 513b can be provided, as illustrated in FIG. 5C, with each of the apical feed ports 513a, 513b located at a different depth at an outer periphery of the projecting portion of an apical insert. Apical feed ports 513a, 513b can also, optionally, be configured in a slot-like configuration (FIG. 5B) such that fluid can be delivered at a number of locations, both horizontally and vertically, within the apical flow channel. A similar configuration can apply to apical effluent ports 515a, 515b.

Figure 5D:
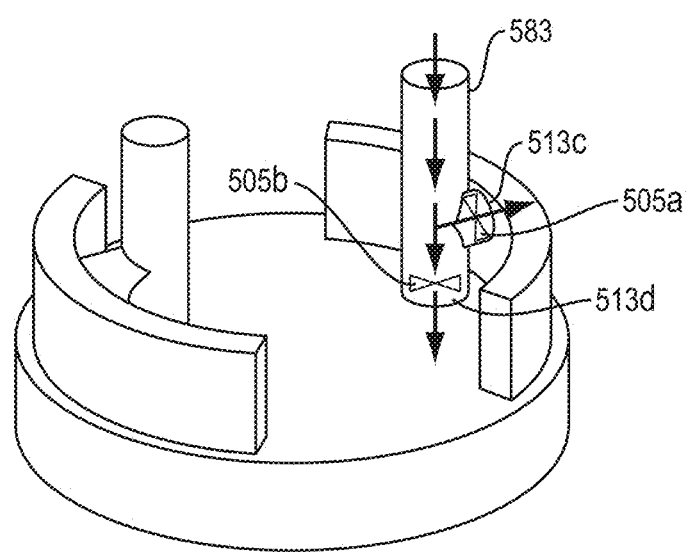
FIG. 5D is a perspective view of another example of a flow geometry from an inlet channel of the apical insert to multiple inlet ports.
Figure 5E:
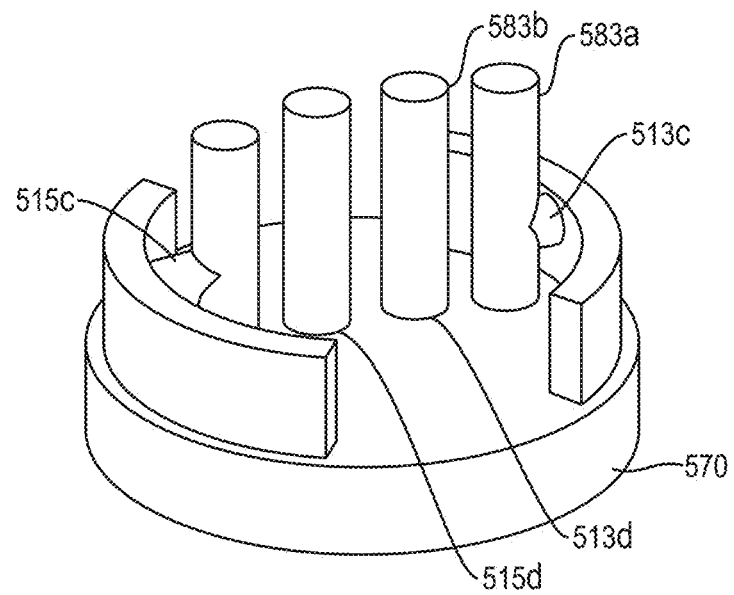
FIG. 5E is a perspective view of an example of a flow geometry having multiple inlet channels.

In yet another configuration, at least two apical feed ports, 513c, 513d can be included, as illustrated in FIG. 5D. One of the apical feed ports 513c can be located at an outer periphery of the protecting portion of an apical insert, and the other of the apical feed ports 513d can be located at an apical surface of the projecting portion of the apical insert. Port configurations in which apical feed ports can provide fluid delivery to varying depths within an apical domain, such as those illustrated in FIGS. 5C and 5D, can be useful for providing varying types of media or varying concentrations of media to different locations within the apical chamber. For example, it may be desirable to deliver liquid media through apical feed ports located on an apical surface of the projecting portion (e.g., apical feed port 513d), while delivering gas, such as oxygen, through apical feed ports located at a periphery of the apical insert (e.g., apical feed port 513c). To control a depth of fluid delivery, optional valves 505a, 505b, can be included at each apical port. Valves can be operated by an optional controller. (FIG. 6C) Alternatively, a number of inlet channels can be provided, as illustrated in FIG. 5E. Each inlet channel, or a subset of a plurality of inlet channels, can terminate in feed ports located at a different location. For example, a first inlet channel 583a can terminate with an apical feed port 513c, located at a periphery of the projecting portion of the insert, and a second inlet channel 583b can terminate with an apical feed port 513d located an apical surface of the projecting portion of the insert. A number of outlet channels 515c, 515d can similarly be provided.

For some applications, it can be desirable to disrupt the apical surface of a cell culture. For example, it can be desirable to physically disturb a mucus layer located on top of a cell culture, which may contain microbes, and evacuate the mucus/microbes from the apical chamber. For such applications, a controller can toggle between valves 505a, 505b. For example, oxygen delivery can generally be provided to a cell culture via delivery from apical feed port located at a periphery of the projecting portion of the insert, while delivery of a fluid to cause mucus/microbe disruption can occur via delivery from an apical feed port located at an apical surface of the insert.

Figure 5F:
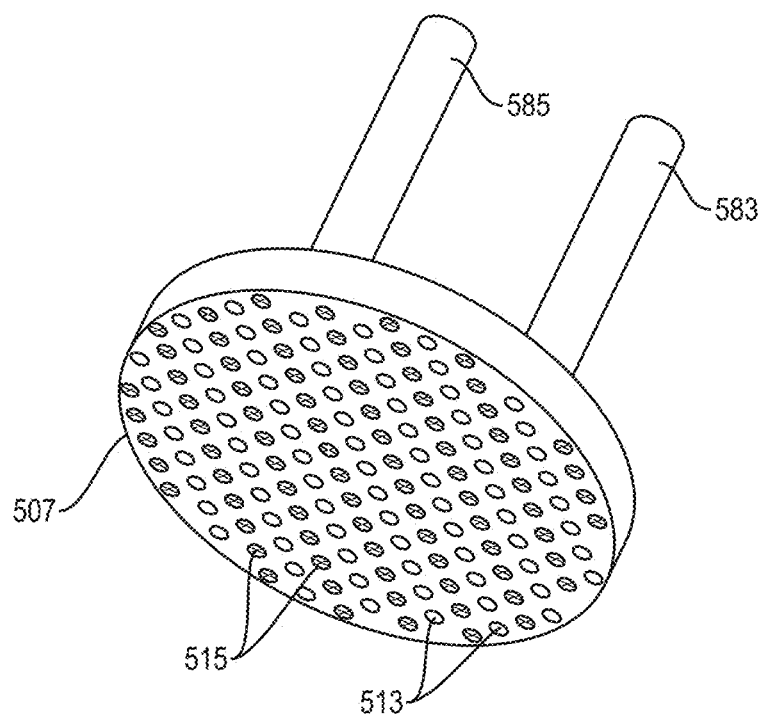
FIG. 5F is a perspective view of an example of a showerhead-type flow geometry.

In another configuration, a plurality of apical feed ports and a plurality of apical effluent ports can be provided. The plurality of apical feed ports 513 and plurality of apical effluent ports 515 can be interspersed at an apical surface 507 of the projecting portion of an apical insert, similar to a showerhead, as illustrated in FIG. 5F.

Figure 6A:
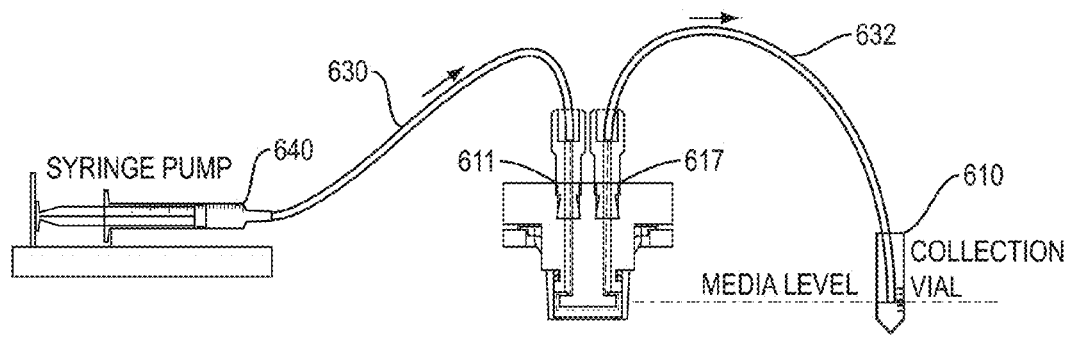
FIG. 6A is a schematic of an example of an apical flow system.
Figure 6B:
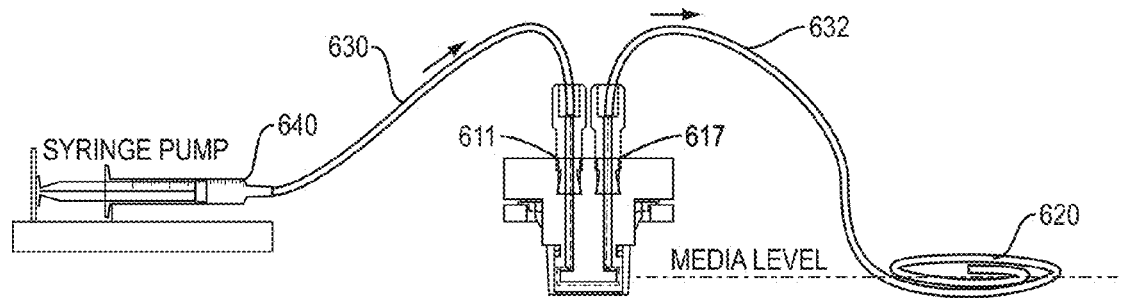
FIG. 6B is a schematic of another example of an apical flow system.
Figure 6C:
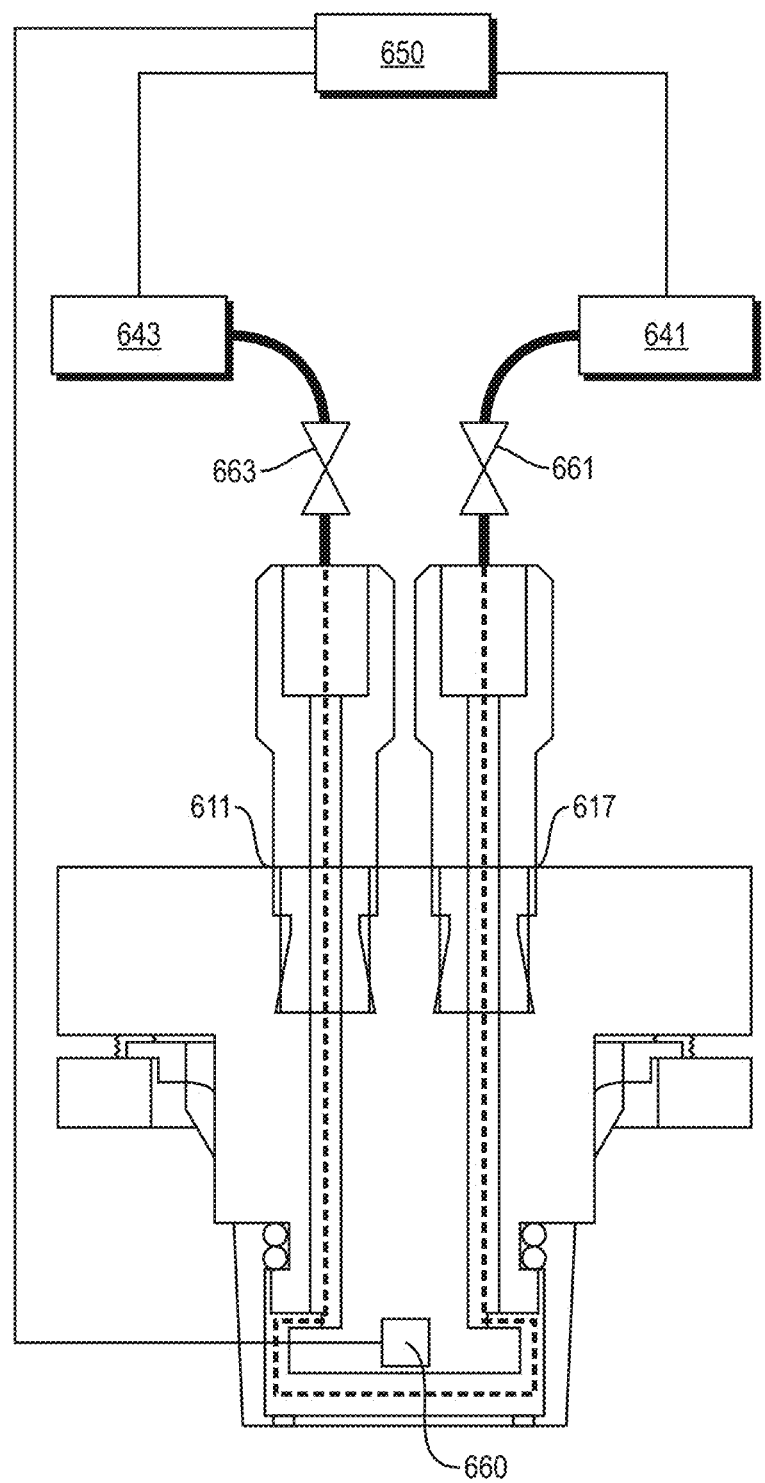
FIG. 6C is a schematic of another example of an apical flow system with a controller.

FIGS. 6A-6C illustrate apical flow systems with additional fluid delivery components. Because the apical domain is sealed by an apical insert, hydrostatic pressure at the cell layer can be affected by a height of outlet media at either a collection vial 610 or coiled tubing 620. To minimize variations in hydrostatic pressure, media collection can occur at approximately the same height as that of a flow channel in an apical delivery system. For example, as shown in FIGS. 6A and 6C, media level within an apical flow channel can be located at approximately the same height (indicated by dashed lines) as a medial level in a collection vial 610, or coiled tubing 620. While a collection vial 610 is simple to set up and provides straightforward collection of media samples, hydrostatic pressure can slowly build up as media height in the collection vial rises, unless the height of the collection vial is adjusted during outlet flow. In contrast, coiled tubing 620 can provide constant hydrostatic pressure; however, retrieving media samples can require extra work on the part of a user as the entire volume of sampling media is contained in a long coiled tube, which can be more difficult to handle than a collection vial.

To create flow, tubing 630 coupled to a fitting at inlet port 611 can be connected to a syringe pump 640, although other methods for inducing a gradual flow (e.g. gravity driven flow) can also be provided. Tubing 632 coupled to a fitting at outlet port 617 can be used to directly collect media (FIG. 6B) or can be further connected to other components, such as a collection vial 610 (FIG. 6A).

Alternatively, or in addition, an apical flow system can include a controller 650, as illustrated in FIG. 6C. Controller 650 can be configured to control flow of a fluid through the apical chamber by controlling valves 661, 663 and/or pumps 641, 643 that are in fluidic communication with an inlet port 611, an outlet port 617, or both. Through control of at least one valve or at least one pump of an apical flow system, a flow of fluid can be supplied to an apical chamber with a substantially even velocity profile across an apical surface of the hanging cell culture insert.

An apical flow system can also include at least one sensor 660 coupled to the apical insert and configured to sense a biological condition at an apical surface of the hanging cell culture insert. The controller 650 can be in communication with the sensor 660 and can be further configured to cause a valve or a pump (not shown) to change state depending upon an output of the sensor 660. For example, sensor 660 can be configured to sense an oxygen concentration in the apical chamber. If a sensed oxygen concentration falls outside of established thresholds, an inlet valve 663 can be opened and a flow of oxygen can be provided. Sensor 660 can, for example, sense an oxygen concentration, a pH, a transepithelial electrical resistance, and/or a temperature. Sensor 660 can also be configured to detect the presence of or a concentration of salts, metabolites, or other signaling molecules, such as cytokines and growth factors, that are released by the cultured cells. More than one sensor can be included in an apical flow system. The controller 650 may be hardware, firmware, or a microcontroller with software that can be loaded from a non-transitory computer-readable medium and executed by the microcontroller to cause a state change to the valve or pump. The software may be any form of software that can cause the microcontroller to perform functions as disclosed hereinabove.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A device for controlling apical flow to a cell culture, comprising:
an apical insert including (i) a projecting portion configured to extend into a cell culture insert to a depth that is less than a depth of the cell culture insert, the projecting portion including an apical surface and at least one peripheral surface, and (ii) a contact surface configured to maintain a spatial relationship between the projecting portion and the cell culture insert, the apical insert defining at least one inlet channel extending from an inlet port to an apical feed port and at least one outlet channel extending from an apical effluent port to an outlet port, the apical feed port and the apical effluent port each being disposed at the at least one peripheral surface of the projecting portion.

2. The device of claim 1, wherein the projecting portion is a cylindrical boss.

3. The device of claim 1, wherein the apical insert includes at least two apical feed ports, one of the apical feed ports being the apical feed port disposed at the peripheral surface of the protecting portion and the other of the apical feed ports located at an apical surface of the projecting portion.

4. The device of claim 1, wherein the apical insert includes at least two apical feed ports, each of the apical feed ports disposed at a different depth at the peripheral surface of the projecting portion.

5. The device of claim 1, further comprising a seal coupled to the projecting portion and configured to seal the projecting portion against an inner perimeter of the cell culture insert.

6. The device of claim 1, further comprising a seal coupled to the contact surface and configured to seal the contact surface against a flange of the cell culture insert.

7. The device of claim 1, further comprising at least one sensor coupled to the projecting portion.

8. The device of claim 7, wherein the at least one sensor is configured to sense a biological condition at an apical surface of the cell culture insert.

9. The device of claim 7, wherein the at least one sensor senses an oxygen concentration, a pH, a transepithelial electrical resistance, a salt concentration, a metabolite concentration, or a temperature.

10. The device of claim 1, wherein the apical feed port is configured to deliver fluid to a vertical volume defined by the at least one peripheral surface of the projecting portion and an inner perimeter of the cell culture insert.

11. The device of claim 1, wherein the apical feed port and the apical effluent port are disposed substantially horizontal to each other on the at least one peripheral surface.

12. The device of claim 1, wherein the apical feed port and the apical effluent port are configured to provide a uniform flow distribution of a fluid to an apical surface of a cell culture.

13. A system for controlling apical flow to a cell culture, comprising:
   a cell culture insert;
   an apical insert including a projecting portion configured to extend into a cell culture insert to a depth that is less than a depth of the cell culture insert, the projecting portion including an apical surface and at least one peripheral surface, and a contact surface configured to maintain a spatial relationship between the projecting portion and the cell culture insert, the apical insert defining at least one inlet channel extending from an inlet port to an apical feed port and at least one outlet channel extending from an apical effluent port to an outlet port, the apical feed port and the apical effluent port each being disposed at the at least one peripheral surface of the projecting portion; and
   at least one seal configured to seal the insert against the cell culture insert.

14. The system of claim 13, further comprising at least one valve in fluidic communication with the inlet port and configured to control flow of a fluid through the inlet channel.

15. The system of claim 13, further comprising at least one pump in fluidic communication with the inlet port, the outlet port, or both and configured to control flow of a fluid through an apical volume defined by the projecting portion and the cell culture insert.

16. The system of claim 13, further comprising a controller configured to control flow of a fluid through an apical chamber defined by the projecting portion and the cell culture insert through control of at least one valve or at least one pump, wherein the at least one valve or at least one pump is in fluidic communication with the inlet port, the outlet port, or both.

17. The system of claim 13, further comprising a controller configured to control at least one valve or at least one pump, in fluidic communication with the inlet port, the outlet port, or both, to supply a flow of a fluid with a substantially even velocity profile across an apical surface of the cell culture insert.

18. The system of claim 13, further comprising:
   at least one sensor coupled to the apical insert and configured to sense a biological condition at an apical surface of the cell culture insert; and
   a controller in communication with the sensor and configured to cause a valve or pump, in fluidic communication with the inlet port or outlet port, to change state as a function of a representation of the biological condition output by the at least one sensor.

* * * * *